United States Patent
Knopff et al.

(10) Patent No.: US 9,926,249 B2
(45) Date of Patent: Mar. 27, 2018

(54) PRINS REACTION ON HINDERED SUBSTRATES

(71) Applicant: Firmenich SA, Geneva (CH)

(72) Inventors: Oliver Knopff, Geneva (CH); Fabien Fonteny, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/321,880

(22) PCT Filed: Jul. 1, 2015

(86) PCT No.: PCT/EP2015/064947
§ 371 (c)(1),
(2) Date: Dec. 23, 2016

(87) PCT Pub. No.: WO2016/001286
PCT Pub. Date: Jan. 7, 2016

(65) Prior Publication Data
US 2017/0129834 A1    May 11, 2017

(30) Foreign Application Priority Data
Jul. 2, 2014 (EP) ...................... 14175359

(51) Int. Cl.
*C07C 29/44* (2006.01)

(52) U.S. Cl.
CPC .......... *C07C 29/44* (2013.01); *C07C 2101/16* (2013.01); *C07C 2601/16* (2017.05)

(58) Field of Classification Search
CPC ............................ C07C 29/44; C07C 2601/16
USPC ........................................................ 568/808
See application file for complete search history.

(56) References Cited

U.S. PATENT DOCUMENTS 3,414,588 A   12/1968   Jones

FOREIGN PATENT DOCUMENTS

EP   2215069 A1   8/2010

OTHER PUBLICATIONS

Ohloff et al., "Zur Stereochemie der Geruchswahrnehmung von 1-Dekalon-Derivaten und ihren oxaanalogen Verbindungen," Helvetica Chimica Acta, 59(4):1140-1157 (1976) (English abstract).
International Search Report and Written Opinion, application PCT/EP2015/064947 dated Sep. 3, 2015.
Hutchinson et al., Can. J. Chem, 62, 1984, 1899-1902.
Kato et al., Tetrahedron 1996, 52, 11, 3921-3932.
Ohloff et al., Helv. Chim. Acta 1976, 59, 4, 1140-1157.
Pamingle et al., Helv. Chim. Acta 1991, 74, 3, 543-548.
Pati, Mukerjee et al., Tetrahedron 2002, 58, 1773-1778.

*Primary Examiner* — Sikarl Witherspoon
(74) *Attorney, Agent, or Firm* — Winston & Strawn LLP

(57) ABSTRACT

The present invention relates to the field of organic synthesis and more specifically it concerns a process for the preparation of homoallylic alcohol derivatives as defined in formula (I) via a reaction of alkene of formula (II) with an aldehyde.

16 Claims, No Drawings

PRINS REACTION ON HINDERED SUBSTRATES

This application is a 371 filing of International Patent Application no. PCT/EP2015/064947 filed Jul. 1, 2015, which claims the benefit of European patent application no. 14175359.0 filed Jul. 2, 2014.

TECHNICAL FIELD

The present invention relates to the field of organic synthesis and more specifically it concerns a process for the preparation of homoallylic alcohol derivatives as defined in formula (I) via a reaction of highly sterically hindered alkene of formula (II) with an aldehyde.

PRIOR ART

Many homoallylic alcohol derivatives as defined in formula (I) are useful products as such or useful intermediates of the preparation of other important raw materials in particular for the perfumery industry (e.g. 2-(2,5,5,8a-tetramethyl-3,4,4a,5,6,7,8,8a-octahydronaphthalen-1-yl)ethan-1-ol). The latter compound is an important intermediate for the preparation of industrially relevant compounds such as Cetalox® (3a,6,6,9a-tetramethyldodecahydronaphtho[2,1-b]furan; origin: Firmenich SA, Geneva, Switzerland) or Ambrox® (mixture of diastereomers of 3a,6,6,9a-tetramethyldodecahydronaphtho[2,1-b]furan; origin: Firmenich SA, Geneva, Switzerland).

Homoallylic compounds of formula (I) have been prepared in the literature, for example, by reduction of the corresponding aldehyde, ester or acid group (e. g. EP 2215069).

Such synthetic approaches require multistep process, which inevitably induce lower efficiency. Therefore, there is still a need for a method to prepare the target compounds in a more efficient way, i.e. which allows obtaining said compounds with good yields and with only one step process. The aim of the present invention is to provide such process by using an inter molecular Prins reaction.

The present compounds (I) have never been reported or suggested in literature as being obtainable by the present process which is based on a Prins type reaction. The absence of antecedent of a Prins reaction performed with highly sterically hindered alkene and an aldehyde, has created a prejudice against the present process, thus discouraging the person skilled in the art. The only example known is an intra molecular reaction leading to ring formation (see *Tetrahedron* 1996, 52 (11), 3921-3932) but intra molecular reactions are known to be much easier than inter molecular reactions and the former cannot be considering as anticipating the latter.

DESCRIPTION OF THE INVENTION

We have now found that the derivatives of formula (I) can be produced in an advantageous manner by means of a Prins type reaction.

Therefore, a first object of the present invention is a process for the preparation of a compound of formula (I)

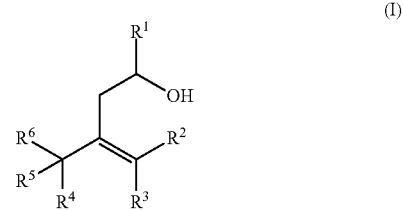

wherein $R^1$ represents a hydrogen atom or a $C_{1-8}$ alkyl group;

each $R^2$, $R^3$, $R^4$, $R^5$ represent, when taken separately, independently from each other, a $C_{1-9}$ linear, branched or cyclic alkyl group optionally substituted by one to two $C_{1-5}$ alkyl groups and optionally comprising one or two functional groups selected amongst ether, ester, carbonyl, amine, amide or alcohol group; $R^2$ and $R^3$ when taken together, represent a $C_{4-11}$ linear, branched or cyclic alkanediyl group optionally comprising one or two functional groups selected amongst ether, ester, carbonyl, amine, amide or alcohol group and/or $R^3$ and $R^4$, when taken together, represent a $C_{2-9}$ linear, branched or cyclic alkanediyl group and/or $R^4$ and $R^5$, when taken together, represent a $C_{4-9}$ linear, branched or cyclic alkanediyl group and/or $R^2$ and $R^5$, when taken together, represent a $C_{2-9}$ linear, branched or cyclic alkanediyl group; and $R^6$ represents a $C_{1-3}$ linear or branched alkyl group;

in the form of any one of its stereoisomers or a mixture thereof;

said process comprising the step of reacting a corresponding compound of formula (II)

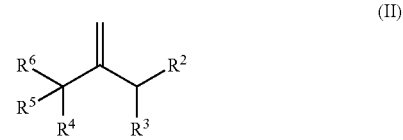

wherein $R^2$, $R^3$, $R^4$, $R^5$ and $R^6$ have the same meaning as in formula (I)

with a compound of formula $R^1CHO$, wherein $R^1$ has the same meaning as in formula (I).

It is understood that by " . . . $R^2$ and $R^3$, when taken together, represent a $C_{2-9}$ linear, branched or cyclic alkanediyl group . . . and/or $R^3$ and $R^4$, when taken together, represent a $C_{2-9}$ linear, branched or cyclic alkanediyl group and/or $R^4$ and $R^5$, when taken together . . . " or the similar, that said group could form a (poly)cyclic alkyl group. In other words compound (II) could be acyclic, monocyclic, bicyclic or tricyclic, e.g. in the case wherein $R^3$ and $R^4$, as well as $R^4$ and $R^5$, are taken together, the compound of formula (II) comprises a bicyclic moiety such as a decalin, e.g. $R^3$, $R^4$ and $R^5$, taken together, represents an alkanetriyl.

According to any one of the above embodiments of the invention, said compounds of formula (II) are $C_9$-$C_{20}$ compounds.

According to any one of the above embodiments of the invention, said compound (I) is compound of formula (III)

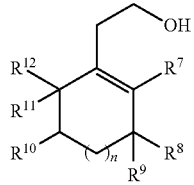
(III)

wherein n is 0 or 1;
each R⁸, R⁹, R¹⁰ represent, when taken separately, independently from each other, a hydrogen atom or a $C_{1-6}$ linear, branched or cyclic alkyl group optionally substituted by one to two $C_{1-3}$ alkyl groups and optionally comprising one or two functional groups selected amongst ether, ester, carbonyl, amine, amide or alcohol group;
each R⁷, R¹¹, R¹² represent, when taken separately, independently from each other, a $C_{1-6}$ linear, branched or cyclic alkyl group optionally substituted by one to two $C_{1-3}$ alkyl groups and optionally comprising one or two functional groups selected amongst ether, ester, carbonyl, amine, amide or alcohol group; R⁷ and R⁸, when taken together, represent a $C_{3-9}$ linear or branched alkanediyl group optionally comprising one or two functional groups selected amongst ether, ester, carbonyl, amine, amide or alcohol group and/or R⁹ and R¹⁰, when taken together, represent a $C_{1-2}$ linear alkanediyl group and/or R¹⁰ and R¹¹, when taken together, represent a $C_{3-9}$ linear or branched alkanediyl group and/or R⁸ and R¹¹, when taken together, represent a $C_{1-3}$ linear or branched alkanediyl group; and
R¹² represents a $C_{1-3}$ linear or branched alkyl group;
in the form of any one of its stereoisomers or a mixture thereof.

According to any one of the above embodiments of the invention, said compound (II) is compound of formula (IV)

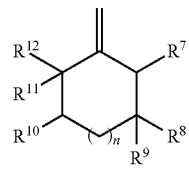
(IV)

wherein n, R⁷, R⁸, R⁹, R¹⁰, R¹¹ and R¹² have the same meaning as in formula (III).

It is understood that by " . . . R⁷ and R⁸, when taken together, represent a $C_{3-9}$ linear or branched alkanediyl group . . . and/or R⁹ and R¹⁰, when taken together, represent a $C_{1-2}$ linear alkanediyl group and/or R¹⁰ and R¹¹, when taken together, represent a $C_{3-9}$ linear or branched alkanediyl group and/or R⁸ and R¹¹, when taken together, . . . " or the similar, that said group could form a (poly)cyclic alkyl group; i.e. compounds (III) and (IV) could be monocyclic, bicyclic or tricyclic, e.g. compounds (III) and (IV) are tricyclic compounds when R⁷ and R⁸, as well as R⁹ and R¹⁰, are taken together.

According to a particular embodiment compounds (III) and (IV) are monocyclic, bicyclic or tricyclic compounds.

Preferably compounds (III) and (IV) are mono cyclic or bicyclic compounds, even more preferably bicyclic compounds. Said compound of formula (IV) can be synthetic or natural. In particular compound of formula (IV) can be a natural sesquiterpene derivative with an exo double-bond, e.g. (3S,3aS,6R)-3,7,7-trimethyl-8-methyleneoctahydro-1H-3a,6-methanoazulene known as zizaene or (7,7-dimethyl-8-methyleneoctahydro-1H-3a,6-methanoazulen-3-yl)methyl acetate which, in the case of R¹ is a hydrogen atom, provides respectively under the process of the invention 2-((3S,3aS,6R)-3,7,7-trimethyl-2,3,4,5,6,7-hexahydro-1H-3a,6-methanoazulen-8-yl)ethan-1-ol or (8-(2-hydroxyethyl)-7,7-dimethyl-2,3,4,5,6,7-hexahydro-1H-3a,6-methanoazulen-3-yl)methyl acetate. Specific and non-limiting examples of synthetic compound of formula (IV) are selected from the list consisting of 1,1,4a,6-tetramethyl-5-methylenedecahydronaphthalene, 1,1,3-trimethyl-2-methylenecyclohexane, 2,3,8a-trimethyl-1-methylenedecahydronaphthalene, 1,3,7,7-tetramethyl-2-methylenebicyclo[2.2.1]heptane and (3,3,4-trimethyl-2-methylenecyclopentyl)methyl acetate which, in the case of R¹ is a hydrogen atom, provide respectively under the process of the invention 2-(2,5,5,8a-tetramethyl-3,4,4a,5,6,7,8,8a-octahydronaphthalen-1-yl)ethan-1-ol, 2-(2,6,6-trimethylcyclohex-1-en-1-yl)ethan-1-ol, (2,3,8a-trimethyl-3,4,4a,5,6,7,8,8a-octahydronaphthalen-1-yl)ethan-1-ol, 2-((1R,4R)-1,3,7,7-tetramethylbicyclo[2.2.1]hept-2-en-2-yl)ethan-1-ol and 2-(2-(hydroxymethyl)-4,5,5-trimethylcyclopent-1-en-1-yl)ethan-1-ol.

According to any embodiments of the invention, and independently of the specific aspects, the compound (III), as well as the corresponding compound (IV), can be in the form of any one of its stereoisomers or mixture thereof. For the sake of clarity by the term stereoisomer it is intended any diastereomer, enantiomer, racemate.

Indeed, the compound (III) or (IV) may have stereogenic centers which can have different stereochemistry (i.e. when two stereogenic centers are present, compound (III) or (IV) can have (R,R) or (R,S) configuration). Each of said stereogenic centers can be in a relative configuration R or S or a mixture thereof or in other words said compound of formula (III) or (IV) can be in a form of pure enantiomer or diastereoisomer, or in a form of a mixture of stereoisomers.

According to a particular embodiment of the invention, the compound of formula (III) is 2-(2,5,5,8a-tetramethyl-3,4,4a,5,6,7,8,8a-octahydronaphthalen-1-yl)ethan-1-ol and the corresponding compound of formula (IV) is 1,1,4a,6-tetramethyl-5-methylenedecahydronaphthalene which have three stereogenic centers being in a configuration R or S or a mixture thereof. In other worlds 1,1,4a,6-tetramethyl-5-methylenedecahydronaphthalene is in the form of an essentially pure stereoisomer or in the form of a mixture of stereoisomers. According to a particular embodiment of the invention, compound of formula (IV) is in the form of a mixture of stereoisomers containing at least 80% of both stereoisomers (4aSR,6SR,8aSR)-1,1,4a,6-tetramethyl-5-methylenedecahydronaphthalene and (4aSR,6RS,8aSR)-1,1,4a,6-tetramethyl-5-methylenedecahydronaphthalene.

Preferably compound of formula (IV) is in the form of a mixture of stereoisomers containing at least 50% of (4aSR,6SR,8aSR)-1,1,4a,6-tetramethyl-5-methylenedecahydronaphthalene. Even more preferably, compound of formula (IV) is in the form of a mixture of stereoisomers containing at least 75% of (4aSR,6SR,8aSR)-1,1,4a,6-tetramethyl-5-methylenedecahydronaphthalene. According to a particular embodiment of the invention, compound (IV) is (4aSR,6SR,8aSR)-1,1,4a,6-tetramethyl-5-methylenedecahydronaphthalene. For the sake of clarity, by the expression "4aSR,6SR,8aSR" it is meant an equimolar mixture of 4aS,6S,8S and 4aR,6R,8R and by the expression "4aSR,6RS,8aSR" it is meant an equimolar mixture of 4aS,6R,8S and 4aR,6S,8R. According to particular a embodiment of the invention, compound (II) is (4aS,6S,8aS)-1,1,4a,6-tetramethyl-5-methylenedecahydronaphthalene.

According to any one of the invention's embodiments, each $R^8$, $R^9$, $R^{10}$ represent, when taken separately, independently from each other, a hydrogen atom or a $C_{1-6}$ linear, branched or cyclic alkyl group optionally substituted by one to two $C_{1-3}$ alkyl groups and optionally comprising one or two functional groups selected amongst ether, ester or carbonyl group; each $R^7$, $R^{11}$, $R^{12}$ represent, independently from each other, a $C_{1-6}$ linear, branched or cyclic alkyl group optionally substituted by one to two $C_{1-3}$ alkyl groups and optionally comprising one or two functional groups selected amongst ether, ester or carbonyl group; $R^7$ and $R^8$, when taken together, represent a $C_{3-9}$ linear or branched alkanediyl group optionally comprising one or two functional groups selected amongst ether, ester or carbonyl group.

According to any one of the invention's embodiments, said $R^7$ group represents a $C_{1-3}$ alkyl group optionally comprising one functional group selected from ether, ester and carbonyl or even preferably a methyl group.

According to any one of the invention's embodiments, said $R^{12}$ group represents a methyl group.

According to any one of the invention's embodiments, said $R^8$ group represents a hydrogen atom or $C_{1-3}$ alkyl group or even preferably a hydrogen atom or a methyl group.

According to any one of the invention's embodiments, said $R^9$ group represents a hydrogen atom or $C_{1-3}$ alkyl group or even preferably a hydrogen atom or a methyl group.

According to any one of the invention's embodiments, said $R^{10}$ group represents a hydrogen atom or $C_{1-3}$ alkyl group or even preferably a hydrogen atom or a methyl group.

According to any one of the invention's embodiments, said $R^{11}$ group represents a $C_{1-3}$ linear or branched alkyl group or even preferably a methyl group.

According to any one of the invention's embodiments, said $R^7$ and $R^8$ when taken together, represent a $C_{3-6}$ linear or branched alkanediyl group or even preferably a $C_4$ branched alkanediyl group.

According to any one of the invention's embodiments, said $R^9$ and $R^{10}$ when taken together, represent a $C_{1-2}$ linear alkanediyl group or even preferably a $C_2$ linear alkanediyl group.

According to any one of the invention's embodiments, said $R^{10}$ and $R^{11}$, when taken together, represent a $C_{3-6}$ linear or branched alkanediyl group or even preferably a $C_6$ branched alkanediyl group.

According to any one of the invention's embodiments, said $R^8$ and $R^{11}$, when taken together, represent a $C_3$ branched alkanediyl group.

According to any one of the invention's embodiments, n is 1.

The compounds of formula (IV) can be prepared by several methods, for example in the case of 1,1,4a,6-tetramethyl-5-methylenedecahydronaphthalene by hydrogenation followed by photolysis of (+)-15,16-dinorlabd-8(20)-en-13-on as described in *Helv. Chim. Acta* 1976, 59 (4), 1140-1157.

As mentioned above, the reaction is carry out in a presence of $R^1$CHO wherein $R^1$ is a hydrogen atom or a $C_1$ to $C_8$ alkyl group. According to any one of the invention's embodiments, $R^1$ is a hydrogen atom, i.e. $R^1$CHO is formaldehyde.

According to any one of the invention's embodiments, formaldehyde is used in different quality grades, i.e. anhydrous formaldehyde or aqueous solution of formaldehyde is used. The aqueous solution may contain at most 15 weight % of water, more preferably the aqueous solution contains at most 10 weight % of water. According to any one of the invention's embodiments, it is used anhydrous formaldehyde. i.e. containing less that 1% w/w of water.

According to any one of the invention's embodiments, the compound of formula $R^1$CHO can be used as such or in the form of a synthetic equivalent.

By the expression "synthetic equivalent", it is meant here a compound which under the reaction conditions of the present invention will release $R^1$CHO. For example, when said $R^1$CHO is formaldehyde, specific and non-limiting examples of such synthetic equivalent are oligomer or polymer form of formaldehyde e.g. 1,3,5-trioxane, paraformaldehyde, or protected formaldehyde e.g. dimethoxymethane or a mixture of formaldehyde and hemiacetal of formaldehyde with alcohol, e.g. Formcel® (trademark from Celanese Chemicals, New-York, USA) which is a mixture of formaldehyde, methoxymethanol, methanol and water.

According to any one of the invention's embodiments, said $R^1$CHO is in the form of paraformaldehyde.

Said $R^1$CHO can be added into the reaction medium of the invention's process in a large range of concentrations. As non-limiting examples, one can cite as $R^1$CHO concentration values those ranging from about 0.5 molar equivalents to about 7 molar equivalents, relative to the amount of the compound of formula (II). Preferably, the $R^1$CHO concentration will be comprised between 1 molar equivalent to 5 molar equivalents, relative to the amount of the compound of formula (II). It goes without saying that the optimum concentration of $R^1$CHO will depend, as the person skilled in the art knows, on the nature of the latter, on the nature of the substrate and of the temperature used during the process, as well as the desired time of reaction.

The Prins reaction in general is known to be promoted by a vast variety of reaction conditions including (and always preferred) a large number of Lewis acid catalysts. Now it was surprisingly found that in the present case, i.e. a highly sterically hindered alkene (II), the thermal conditions, i.e. uncatalyzed, are preferred.

In the invention's process, the reaction between compound (II) and compound $R^1$CHO can be promoted only under thermal conditions, which is very counterintuitive since it is known that under such conditions the mechanism is pericyclic (i.e. highly sensible to the steric hindrance) and reversible (i.e. difficult to achieve good yields) (see March's "Advanced Organic Chemistry", $5^{th}$ edition 2001, pg 1242). Furthermore, under the thermal reaction conditions of the Prins reaction, the competitive reaction which is the isomerization of the exo double bond of compound of formula (II) is expected to be significant.

According to any one of the invention's embodiments, the invention's process is carried out at a temperature comprised between 130° C. and 300° C. In particular, the temperature is in the range between 160° C. and 230° C. Of course, a person skilled in the art is also able to select the preferred temperature as a function of the melting and boiling point of the starting and final products as well as the desired time of reaction or conversion.

According to any one of the invention's embodiments, the process of the invention can also be carried out optionally in the presence of carboxylic derivative selected amongst a $C_{2-8}$ carboxylic acid, $C_{4-16}$ carboxylic anhydride or a mixture of said carboxylic acid and said carboxylic anhydride. Indeed it has been found that such carboxylic derivative improve the yields of process and/or allows to lower the amount of $R^1CHO$ required in the process.

As non-limiting examples of such carboxylic derivative, one can site acetic acid or propionic acid, acetic anhydride or a mixture of acetic acid and acetic anhydride.

The carboxylic derivative can be added into the reaction medium of the invention's process in a large range of concentrations. As non-limiting examples, one can cite as carboxylic derivative concentration values those ranging from about 0.0 molar equivalent to about 5 molar equivalents, relative to the amount of compound of formula (II). Preferably, the carboxylic derivative concentration will be comprised between 0.5 molar equivalents to 2.5 molar equivalents or even between 0.8 molar equivalents to 2.2 molar equivalents, relative to the amount of compound of formula (II).

When the carboxylic derivative is in the form of mixture of carboxylic acid and carboxylic anhydride, the carboxylic acid and carboxylic anhydride are preferably used in a respective molar ratio comprised between 0.05:1 and 2:1, more preferably between 0.1:1 and 0.5:1. It goes without saying that the optimum concentration of carboxylic derivative will depend, as the person skilled in the art knows, on the nature of the latter, on the nature of the substrate and the temperature as well as the desired time of reaction.

The process of the invention can be followed by a hydrolysis step in order to convert side products formed during the process (i.e. formate, acetate, methoxymethyl ether) into alcohol of formula (I).

The reaction can be carried out in the presence or absence of a solvent. When a solvent is required or used for practical reasons, then any solvent current in such reaction type can be used for the purposes of the invention. Non-limiting examples include methanol, ethanol, cyclohexane, THF, Me-THF, MTBE, DME, $Et_2O$, toluene, ethyl acetate, butanone, dichloromethane, dodecane. The choice of the solvent is a function of the nature of the substrate and of the carboxylic derivative and the person skilled in the art is well able to select the solvent most convenient in each case to optimize the reaction.

Starting material (in the form of a mixture of (4aSR,6SR,8aSR)-1,1,4a,6-tetramethyl-5-methylenedecahydronaphthalene and (4aSR,6RS,8aSR)-1,1,4a,6-tetramethyl-5-methylenedecahydronaphthalene in a ratio 78/22) was obtained according to *Helv. Chim. Acta* 1976, 59 (4), 1140-1157. The preparation of other starting materials are reported herebelow in examples part.

EXAMPLES

The invention will now be described in further details by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Preparation of 2-((4aSR,8aSR)-2,5,5,8a-tetramethyl-3,4,4a,5,6,7,8,8a-octahydronaphthalen-1-yl)ethan-1-ol Without Carboxylic Derivative In a 10 mL autoclave (Premex MED278, steel bomb), a mixture of (4aSR,6SR,8aSR)-1,1,4a,6-tetramethyl-5-methylenedecahydronaphthalene and (4aSR,6RS,8aSR)-1,1,4a,6-tetramethyl-5-methylenedecahydronaphthalene (80/20, 14.54 mmol), 1.5 mL toluene and paraformaldehyde (43.6 mmol) was heated 2 h at 190° C. under stirring. After cooling down to room temperature, the mixture was stirred in a round bottom flask in 20 mL methanol and KOH (7.27 mmol) was added. After one hour EtOAc was added and the organic layer was washed once with water and once with brine. The aqueous layer was extracted once with EtOAc and the combined organic layers were dried over $MgSO_4$ and filtered. The solvent was removed under vacuum and the residue was purified by flash chromatography, which afforded 2-((4aSR,8aSR)-2,5,5,8a-tetramethyl-3,4,4a,5,6,7,8,8a-octahydronaphthalen-1-yl)ethan-1-ol (47% yield) and the starting material, i.e. a mixture of (4aSR,6SR,8aSR)-1,1,4a,6-tetramethyl-5-methylenedecahydronaphthalene and (4aSR,6RS,8aSR)-1,1,4a,6-tetramethyl-5-methylenedecahydronaphthalene was recovered (61/39, 7.49 mmol, 51% yield).

$^1$H-NMR: 0.83 (s, 3H), 0.88 (s, 3H), 0.95 (s, 3H), 1.04-2.10 (m, 12H), 1.61 (s, 3H), 2.31 (m, 2H), 3.60 (m, 2H).

$^{13}$C-NMR: 19.0, 19.0, 19.9, 20.1, 21.7, 31.5, 33.3, 33.3, 33.7, 37.2, 38.7, 41.7, 51.7, 62.6, 128.5, 136.2.

1% of corresponding alcohol protected with methoxymethyl ether was isolated and can be easily hydrolyzed into the corresponding alcohol.

$^{13}$C-NMR: 19.0, 19.0, 19.7, 20.0, 21.7, 28.4, 33.3, 33.3, 33.7, 37.0, 38.7, 41.8, 51.8, 55.1. 67.6, 96.3, 128.0, 136.5.

In the Presence of Mixture of Carboxylic Acid and Carboxylic Anhydride

In a 10 mL autoclave (Premex MED278, steel bomb), a mixture of (4aSR,6SR,8aSR)-1,1,4a,6-tetramethyl-5-methylenedecahydronaphthalene and (4aSR,6RS,8aSR)-1,1,4a,6-tetramethyl-5-methylenedecahydronaphthalene (78/22, 19.37 mmol), paraformaldehyde (56.2 mmol), AcOH (3.88 mmol) and $Ac_2O$ (19.38 mmol) was heated 16 h at 182° C. under stirring. After cooling down to room temperature, the mixture was stirred in a round bottom flask in 50 mL methanol and KOH (9.69 mmol) was added. After 30 min AcOEt was added and the organic layer was washed with water and with brine. The aqueous layer was extracted with AcOEt and the combined organic layers were dried over $MgSO_4$ and filtered. The solvent was removed under vacuum and the residue was purified by flash chromatography, which afforded 2-((4aSR,8aSR)-2,5,5,8a-tetramethyl-3,4,4a,5,6,7,8,8a-octahydronaphthalen-1-yl)ethan-1-ol (53% yield) and the starting material (4aSR,6RS,8aSR)-1,1,4a,6-tetramethyl-5-methylenedecahydronaphthalene was recovered (2.53 mmol, 13% yield). 4.7% of the corresponding alcohol protected with methoxymethyl ether were isolated and can be easily hydrolyzed into the corresponding alcohol.

In the Presence of a Carboxylic Anhydride

In a 10 mL autoclave (Premex MED278, steel bomb), a mixture of (4aSR,6SR,8aSR)-1,1,4a,6-tetramethyl-5-methylenedecahydronaphthalene and (4aSR,6RS,8aSR)-1,1,4a,6-tetramethyl-5-methylenedecahydronaphthalene (80/20, 19.38 mmol), paraformaldehyde (58.1 mmol) and $Ac_2O$ (19.38 mmol) was heated 10 h at 180° C. under stirring.

After cooling down to room temperature, the mixture was stirred in a round bottom flask in 50 mL methanol and KOH (48.5 mmol) was added. After 60 min AcOEt was added and the organic layer was washed with water and with brine. The aqueous layer was extracted with AcOEt and the combined organic layers were dried over MgSO$_4$ and filtered. The solvent was removed under vacuum and the residue was purified by flash chromatography, which afforded 2-((4aSR,8aSR)-2,5,5,8a-tetramethyl-3,4,4a,5,6,7,8,8a-octahydronaphthalen-1-yl)ethan-1-ol (61% yield) and the starting material (4aSR,6RS,8aSR)-1,1,4a,6-tetramethyl-5-methylenedecahydronaphthalene was recovered (3.88 mmol, 20% yield).

3% of the corresponding alcohol protected with methoxymethyl ether were isolated and can be easily hydrolyzed into the corresponding alcohol.

In the Presence of Carboxylic Acid

In a 10 mL autoclave (Premex MED278, steel bomb), a mixture of (4aSR,6SR,8aSR)-1,1,4a,6-tetramethyl-5-methylenedecahydronaphthalene and (4aSR,6RS,8aSR)-1,1,4a,6-tetramethyl-5-methylenedecahydronaphthalene (78/22, 19.37 mmol), paraformaldehyde (29.1 mmol) and AcOH (19.38 mmol) was heated 5 h at 185° C. under stirring. After cooling down to room temperature, the mixture was stirred in a round bottom flask in 25 mL methanol and 1.5 g KOH was added. After 16 h AcOEt was added and the organic layer was washed with water and with brine. The aqueous layer was extracted with AcOEt and the combined organic layers were dried over MgSO$_4$ and filtered. The solvent was removed under vacuum and the residue was purified by flash chromatography, which afforded 2-((4aSR,8aSR)-2,5,5,8a-tetramethyl-3,4,4a,5,6,7,8,8a-octahydronaphthalen-1-yl)ethan-1-ol (41% yield) and the starting material (4aSR,6RS,8aSR)-1,1,4a,6-tetramethyl-5-methylenedecahydronaphthalene was recovered (3.65 mmol, 19% yield). 1% of the corresponding alcohol protected with methoxymethyl ether were isolated and can be easily hydrolyzed into the corresponding alcohol.

Example 2

Comparative examples to prepare 2-((4aSR,8aSR)-2,5,5,8a-tetramethyl-3,4,4a,5,6,7,8,8a-octahydronaphthalen-1-yl)ethan-1-ol using Lewis acid In a 10 mL autoclave (Premex MED278, steel bomb), a mixture of (4aSR,6SR,8aSR)-1,1,4a,6-tetramethyl-5-methylenedecahydronaphthalene and (4aSR,6RS,8aSR)-1,1,4a,6-tetramethyl-5-methylenedecahydronaphthalene (44/55, 19.19 mmol) and paraformaldehyde (19.38 mmol) and a Lewis Acid (0.96 mmol) was heated 16 h under stirring with a magnetic bar. After cooling down to room temperature the product yield and conversion was determined by GC.

TABLE 1

Preparation of 2-((4aSR,8aSR)-2,5,5,8a-tetramethyl-3,4,4a,5,6,7,8,8a-octahydronaphthalen-1-yl)ethan-1-ol using various Lewis acid

| Entry | Temperature (° C.) | Lewis Acid | Conversion | Yield |
|---|---|---|---|---|
| 1 | 195° C. | ZnBr$_2$ | 100% | <1% |
| 2 | 130° C. | ZnCl$_2$ | 51% | <1% |
| 3 | 130° C. | FeCl$_3$ | 100% | <1% |

Example 3

Preparation of 2-((3S,3aS,6R)-3,7,7-trimethyl-2,3,4,5,6,7-hexahydro-1H-3a,6-methanoazulen-8-yl)ethanol Without Carboxylic Derivative In a 10 mL autoclave (Premex MED278, steel bomb), (3S,3aS,6R,8aS)-3,7,7-trimethyl-8-methyleneoctahydro-1H-3a,6-methanoazulene (obtained as reported in *Tetrahedron* 2002, 58, 1773-1778) (10.57 mmol), 1.5 mL toluene and paraformaldehyde (44.0 mmol) were heated 3 h at 195° C. under stirring. After cooling down to room temperature, the mixture was stirred in a round bottom flask in 20 mL methanol and KOH (7.34 mmol) was added. After one hour EtOAc was added and the organic layer was washed once with water and once with brine. The aqueous layer was extracted once with EtOAc and the combined organic layers were dried over MgSO$_4$ and filtered. The solvent was removed under vacuum and the residue was purified by flash chromatography, which afforded 2-((3S,3aS,6R)-3,7,7-trimethyl-2,3,4,5,6,7-hexahydro-1H-3a,6-methanoazulen-8-yl)ethanol (3.92 mmol, yield 37%) and the starting material (3S,3aS,6R,8aS)-3,7,7-trimethyl-8-methyleneoctahydro-1H-3a,6-methanoazulene was recovered (5.59 mmol, 53% yield).

$^1$H-NMR: 0.84 (d, J=9.6 Hz, 3H), 1.00 (s, 3H), 1.01 (s, 3H), 1.28-1.37 (m, 3H), 1.52-1.83 (m, 6H), 1.84-1.86 (m, 1H), 1.87-1.94 (m, 1H), 2.15-2.32 (m, 4H), 3.54-3.63 (m, 2H).

$^{13}$C-NMR: 17.2, 24.8, 25.5, 27.1, 29.4, 32.1, 32.4, 34.4, 38.9, 40.0, 40.8, 48.0, 54.0, 62.2, 128.0, 146.6.

In the Presence of a Carboxylic Anhydride

In a 10 mL autoclave (Premex MED278, steel bomb), (3S,3aS,6R,8aS)-3,7,7-trimethyl-8-methyleneoctahydro-1H-3a,6-methanoazulene (obtained as reported in *Tetrahedron* 2002, 58, 1773-1778) (7.34 mmol), paraformaldehyde (29.4 mmol) and Ac$_2$O (9.79 mmol) were heated 10 h at 180° C. under stirring. After cooling down to room temperature, the mixture was stirred in a round bottom flask in 20 mL methanol and KOH (24.47 mmol) were added. After 60 min AcOEt was added and the organic layer was washed with water and with brine. The aqueous layer was extracted with AcOEt and the combined organic layers were dried over MgSO$_4$ and filtered. The solvent was removed under vacuum and the residue was purified by flash chromatography, which afforded 2-((3S,3aS,6R)-3,7,7-trimethyl-2,3,4,5,6,7-hexahydro-1H-3a,6-methanoazulen-8-yl)ethanol (2.68 mmol, yield 37%) and the starting material (3S,3aS,6R,8aS)-3,7,7-trimethyl-8-methyleneoctahydro-1H-3a,6-methanoazulene was recovered (4.09 mmol, 56% yield).

Example 4

Preparation of (S)-2-(2-(hydroxymethyl)-4,5,5-trimethylcyclopent-1-en-1-yl)ethan-1-ol Without Carboxylic Derivative In a 10 mL autoclave (Premex MED278, steel bomb), ((1S,4S)-3,3,4-trimethyl-2-methylenecyclopentyl)methyl acetate (obtained as reported in *Helv. Chim. Acta* 1991, 74 (3), 543-548) (10.27 mmol), 1.5 mL toluene and paraformaldehyde (45.9 mmol) were heated 6 h at 180° C. under stirring. After cooling down to room temperature, the mixture was stirred in a round bottom flask in 10 mL methanol and KOH (7.64 mmol) was added. After one hour EtOAc was added and the organic layer was washed once with water and once with brine. The aqueous layer was extracted once with EtOAc and the combined organic layers were dried over MgSO$_4$ and filtered. The solvent was removed under vacuum and the residue was purified by flash chromatography, which afforded (S)-2-(2-(hydroxymethyl)-4,5,5-trimethylcyclopent-1-en-1-yl)ethan-1-ol (4.52 mmol, 44% yield) and deprotected starting material ((1S,4S)-3,3,4-trimethyl-2-methylenecyclopentyl)methanol was recovered (3.03 mmol, 30% yield).

$^1$H-NMR: 0.77 (s, 3H), 0.93 (d, J=4.6 Hz, 3H), 0.98 (s, 3H), 1.83-1.89 (m, 1H), 1.95-2.01 (m, 1H), 2.21-2.28 (m, 1H), 2.39-2.46 (m, 2H), 3.32 (brs, 1H), 3.55-3.61 (m, 1H), 3.64-3.69 (m, 1H), 4.03-4.12 (m, 2H).

$^{13}$C-NMR: 14.0, 20.3, 26.0, 28.4, 40.3, 43.4, 48.9, 59.1, 61.3, 136.9, 143.8.

In the Presence of a Carboxylic Anhydride

In a 10 mL autoclave (Premex MED278, steel bomb), ((1S,4S)-3,3,4-trimethyl-2-methylenecyclopentyl)methyl acetate (obtained as reported in *Helv. Chim. Acta* 1991, 74 (3), 543-548) (10.27 mmol), paraformaldehyde (45.9 mmol) and Ac$_2$O (15.28 mmol) were heated 10 h at 180° C. under stirring. After cooling down to room temperature, the mixture was stirred in a round bottom flask in 20 mL methanol and KOH (38.2 mmol) was added. After 60 min AcOEt was added and the organic layer was washed with water and with brine. The aqueous layer was extracted with AcOEt and the combined organic layers were dried over MgSO$_4$ and filtered. The solvent was removed under vacuum and the residue was purified by flash chromatography, which afforded (S)-2-(2-(hydroxymethyl)-4,5,5-trimethylcyclopent-1-en-1-yl)ethan-1-ol (5.03 mmol, 49% yield) and deprotected starting material ((1S,4S)-3,3,4-trimethyl-2-methylenecyclopentyl)methanol was recovered (2.59 mmol, 25% yield).

Example 5

Preparation of 2-((3RS,4aRS,8aRS)-2,3,8a-trimethyl-3,4,4a,5,6,7,8,8a-octahydronaphthalen-1-yl)ethan-1-ol Preparation of Starting Material A mixture of the ketones (2SR,3RS,4aRS,8aRS)-2,3,8a-trimethyloctahydronaphthalen-1(2H)-one and (2RS,3RS,4aRS,8aRS)-2,3,8a-trimethyloctahydronaphthalen-1(2H)-one was prepared via a Diels Alder reaction and hydrogenation of the double bond (according to WO 2007/031904) as a 3:2 mixture of diasteriomers.

The above mixture of ketone was treated under Wittig condition following the general procedure below:

Potassium 2-methylpropan-2-olate (61.8 mmol) and methyltriphenylphosphonium bromide (64.3 mmol) were heated at reflux in 200 mL toluene for 2 hours. Then the starting ketone (51.5 mmol) was added dropwise at refluxing temperature. The mixture was stirred at reflux until complete conversion of the starting ketone. After cooling down to room temperature water was added and the layers were separated. The aqueous layer was extracted twice with EtOAc and the combined organic layers were washed with brine, dried over MgSO$_4$ and filtered. The solvent was removed under vacuum to afford yellow oil. Pentane was added and the crystallized solid was separated by filtration. The solid was extracted several times with pentane and the combined organic layers were concentrated after filtration under vacuum and purified by flash chromatography.

A mixture (2SR,3RS,4aRS,8aRS)-2,3,8a-trimethyl-1-methylenedecahydronaphthalene and (2RS,3RS,4aRS,8aRS)-2,3,8a-trimethyl-1-methylenedecahydronaphthalene (83/17)) was obtained according to above the general procedure:

$^1$H-NMR (major diastereoisomer): 0.92 (d, J=6.2 Hz, 3H), 1.04 (d, J=6.5 Hz, 3H), 1.09 (s, 3H), 1.20-1.54 (m, 8H), 1.54-1.60 (m, 1H), 1.64-1.70 (m, 1H), 1.70-1.78 (m, 1H), 1.92-1.97 (m, 1H), 1.98-2.04 (m, 1H), 4.80 (s, 1H), 4.91 (s, 1H).

$^{13}$C NMR (major diastereomer): 15.8, 21.5, 22.6, 27.5, 29.5, 30.9, 34.3, 37.9, 38.3, 40.0, 40.5, 44.4, 106.5, 155.4.

Preparation of 2-((3RS,4aRS,8aRS)-2,3,8a-trimethyl-3,4,4a,5,6,7,8,8a-octahydronaphthalen-1-yl)ethan-1-ol without carboxylic derivative In a 10 mL autoclave (Premex MED278, steel bomb), a mixture of (2SR,3RS,4aRS,8aRS)-2,3,8a-trimethyl-1-methylenedecahydronaphthalene and (2RS,3RS,4aRS,8aRS)-2,3,8a-trimethyl-1-methylenedecahydronaphthalene (83/17, 15.6 mmol), 1.5 mL toluene and paraformaldehyde (46.8 mmol) was heated 6 h at 180° C. under stirring. After cooling down to room temperature, the mixture was stirred in a round bottom flask in 10 mL methanol and KOH (7.80 mmol) was added. After one hour EtOAc was added and the organic layer was washed once with water and once with brine. The aqueous layer was extracted once with EtOAc and the combined organic layers were dried over MgSO$_4$ and filtered. The solvent was removed under vacuum and the residue was purified by flash chromatography, which afforded 2-((3RS,4aRS,8aRS)-2,3,8a-trimethyl-3,4,4a,5,6,7,8,8a-octahydronaphthalen-1-yl)ethan-1-ol (4.68 mmol, 30% yield) and the starting material, i.e. a mixture of (2SR,3RS,4aRS,8aRS)-2,3,8a-trimethyl-1-methylenedecahydronaphthalene and (2RS,3RS,4aRS,8aRS)-2,3,8a-trimethyl-1-methylenedecahydronaphthalene was recovered (78/22, 8.42 mmol, 54% yield).

$^1$H-NMR (55° C.): 1.01 (d, J=6.8 Hz, 3H), 1.05 (s, 3H), 1.22-1.28 (m, 2H), 1.29-1.51 (m, 7H), 1.56-1.64 (m, 2H), 1.66 (s, 3H), 1.70-1.75 (m, 1H), 2.01-2.07 (m, 1H), 2.27-2.33 (m, 1H), 2.36-2.43 (m, 1H), 3.59-3.64 (m, 2H).

$^{13}$C-NMR (55° C.): 18.4, 20.7, 23.2, 24.2, 27.6, 28.8, 32.3, 33.6, 34.1, 35.7, 38.5, 38.9, 62.6, 133.3, 134.1.

Preparation of 2-((3RS,4aRS,8aRS)-2,3,8a-trimethyl-3,4,4a,5,6,7,8,8a-octahydronaphthalen-1-yl)ethan-1-ol in the presence of a carboxylic anhydride In a 10 mL autoclave (Premex MED278, steel bomb), a mixture of (2SR,3RS,4aRS,8aRS)-2,3,8a-trimethyl-1-methylenedecahydronaphthalene and (2RS,3RS,4aRS,8aRS)-2,3,8a-trimethyl-1-methylenedecahydronaphthalene (83/17, 15.6 mmol), paraformaldehyde (46.8 mmol) and Ac$_2$O (15.6 mmol) was heated 10 h at 180° C. under stirring. After cooling down to room temperature, the mixture was stirred in a round bottom flask in 20 mL methanol and KOH (39.0 mmol) was added. After 10 hours EtOAc was added and the organic layer was washed once with water and once with brine. The aqueous layer was extracted once with EtOAc and the combined organic layers were dried over MgSO$_4$ and filtered. The solvent was removed under vacuum and the residue was purified by flash chromatography, which afforded 2-((3RS,4aRS,8aRS)-2,3,8a-trimethyl-3,4,4a,5,6,7,8,8a-octahydronaphthalen-1-yl)ethan-1-ol (4.67 mmol, yield 30%) and the starting material, i.e. a mixture of (2SR,3RS,4aRS,8aRS)-2,3,8a-trimethyl-1-methylenedecahydronaphthalene and (2RS,3RS,4aRS,8aRS)-2,3,8a-trimethyl-1-methylenedecahydronaphthalene was recovered (75/25, 8.07 mmol, 52% yield).

Example 6

Preparation of 2-((1R,4R)-1,3,7,7-tetramethylbicyclo[2.2.1]hept-2-en-2-yl)ethan-1-ol Preparation of Starting Material A mixture of the ketones (1R,3R,4R)-1,3,7,7-tetramethylbicyclo[2.2.1]heptan-2-one and (1R,3S,4R)-1,3,7,7-tetramethylbicyclo[2.2.1]heptan-2-one was obtained from (1R,4R)-1,7,7-trimethylbicyclo[2.2.1]heptan-2-one ((+)-Camphor) according to Can. J. Chem, 62, 1984, 1899-1902 (Methylation) as a 77:22 mixture.

The above mixture of ketone was treated under Wittig condition following the general procedure described in example 5 to afford a mixture of (1R,3R,4R)-1,3,7,7-tetramethyl-2-methylenebicyclo[2.2.1]heptane and (1R,3S,4R)-1,3,7,7-tetramethyl-2-methylenebicyclo[2.2.1]heptane (78/22)).

$^1$H-NMR (major isomer): 0.82 (s, 3H), 0.86 (s, 3H), 0.91 (s, 3H), 1.15 (d, J=7.1 Hz, 3H), 1.17-1.20 (m, 1H), 1.27-1.33 (m, 1H), 1.50-1.58 (m, 2H), 1.76-1.83 (m, 1H), 2.11-2.17 (m, 1H), 4.64 (d, J=2.4 Hz, 1H), 4.69 (d, J=2.4 Hz, 1H).

$^1$H-NMR (Characteristic signals of the minor isomer): 0.78 (s, 3H), 0.88 (s, 3H), 0.92 (s, 3H), 1.05 (d, J=6.7 Hz, 3H), 4.61 (d, J=2.1 Hz, 1H), 4.66 (d, J=2.9 Hz, 1H).

$^{13}$C NMR (major isomer): 12.7, 20.1, 20.5, 21.5, 29.9, 34.0, 43.3, 47.0, 51.4, 52.2, 99.4, 166.3.

Preparation of 2-((1R,4R)-1,3,7,7-tetramethylbicyclo[2.2.1]hept-2-en-2-yl)ethan-1-ol without carboxylic derivative In a 10 mL autoclave (Premex MED278, steel bomb), a mixture of (1R,3R,4R)-1,3,7,7-tetramethyl-2-methylenebicyclo[2.2.1]heptane and (1R,3S,4R)-1,3,7,7-tetramethyl-2-methylenebicyclo[2.2.1]heptane ((78/22), 14.61 mmol), 1.5 mL toluene and paraformaldehyde (43.8 mmol) was heated 2 h at 180° C. under stirring. After cooling down to room temperature, the mixture was stirred in a round bottom flask in 10 mL methanol and KOH (7.30 mmol) were added. After one hour EtOAc was added and the organic layer was washed once with water and once with brine. The aqueous layer was extracted once with EtOAc and the combined organic layers were dried over MgSO$_4$ and filtered. The solvent was removed under vacuum and the residue was purified by flash chromatography, which afforded 2-((1R,4R)-1,3,7,7-tetramethylbicyclo[2.2.1]hept-2-en-2-yl)ethan-1-ol (4.99 mmol, yield 27%) and the starting material, i.e. a mixture of (1R,3R,4R)-1,3,7,7-tetramethyl-2-methylenebicyclo[2.2.1]heptane and (1R,3S,4R)-1,3,7,7-tetramethyl-2-methylenebicyclo[2.2.1]heptane was recovered ((84/15)), 5.23 mmol, yield 29%).

$^1$H-NMR: 0.74 (s, 3H), 0.76 (s, 3H), 0.90-1.01 (m, 2H), 0.97 (s, 3H), 1.53-1.57 (m, 1H) 1.68 (s, 3H), 1.74-1.80 (m, 1H), 2.02 (d, J=3.8 Hz, 1H), 2.23-2.32 (m, 2H), 3.57 (t, J=6.7 Hz, 2H).

$^{13}$C-NMR: 12.0, 12.8, 19.4, 19.5, 24.8, 28.9, 33.8, 54.8, 54.9, 56.8, 61.5, 135.2, 139.5.

What is claimed is:

1. Process for the preparation of a compound of formula (I)

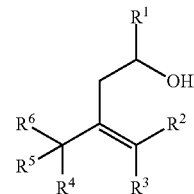

wherein $R^1$ represents a hydrogen atom or a $C_{1-8}$ alkyl group;
each $R^2$, $R^3$, $R^4$, $R^5$ represent, when taken separately, independently from each other, a $C_{1-9}$ linear, branched or cyclic alkyl group optionally substituted by one to two $C_{1-5}$ alkyl groups and optionally comprising one or two functional groups of an ether, ester, carbonyl, amine, amide or alcohol group; $R^2$ and $R^3$, when taken together, represent a $C_{4-11}$ linear, branched or cyclic alkanediyl group optionally comprising one or two functional groups of an ether, ester, carbonyl, amine, amide or alcohol group and/or $R^3$ and $R^4$, when taken together, represent a $C_{2-9}$ linear, branched or cyclic alkanediyl group and/or $R^4$ and $R^5$, when taken together, represent a $C_{4-9}$ linear, branched or cyclic alkanediyl group and/or $R^2$ and $R^5$, when taken together, represent a $C_{2-9}$ linear, branched or cyclic alkanediyl group; and
$R^6$ represents a $C_{1-3}$ linear or branched alkyl group;
in the form of any one of its stereoisomers or a mixture thereof;
said process comprising the step of reacting a corresponding compound of formula (II)

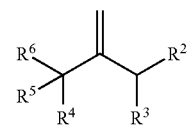

wherein $R^2$, $R^3$, $R^4$, $R^5$ and $R^6$ have the same meaning as in formula (I) with a compound of formula $R^1$CHO, wherein $R^1$ has the same meaning as in formula (I).

2. A process according to claim 1, wherein the compound of formula (II) are $C_9$-$C_{20}$ compounds.

3. A process according to claim 1, wherein the compound of formula (I) is compound of formula (III)

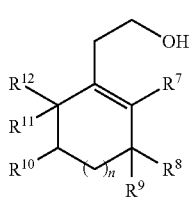

wherein n is 0 or 1;
each $R^8$, $R^9$, $R^{10}$ represent, when taken separately, independently from each other, a hydrogen atom or a $C_{1-6}$ linear, branched or cyclic alkyl group optionally substituted by one to two $C_{1-3}$ alkyl groups and optionally comprising one or two functional groups of an ether, ester, carbonyl, amine, amide or alcohol group;

each $R^7$, $R^{11}$, $R^{12}$ represent, when taken separately, independently from each other, a $C_{1-6}$ linear, branched or cyclic alkyl group optionally substituted by one to two $C_{1-3}$ alkyl groups and optionally comprising one or two functional groups of an ether, ester, carbonyl, amine, amide or alcohol group; $R^7$ and $R^8$, when taken together, represent a $C_{3-9}$ linear or branched alkanediyl group optionally comprising one or two functional groups of an ether, ester, carbonyl, amine, amide or alcohol group and/or $R^9$ and $R^{10}$, when taken together, represent a $C_{1-2}$ linear alkanediyl group and/or $R^{10}$ and $R^{11}$, when taken together, represent a $C_{3-9}$ linear or branched alkanediyl group and/or $R^8$ and $R^{11}$, when taken together, represent a $C_{1-3}$ linear or branched alkanediyl group; and $R^{12}$ represents a $C_{1-3}$ linear or branched alkyl group;

in the form of any one of its stereoisomers or a mixture thereof.

4. A process according to claim 1, wherein the compound of formula (II) is compound of formula (IV)

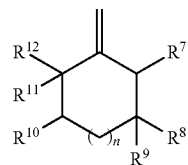

(IV)

wherein n, $R^7$, $R^8$, $R^9$, $R^{10}$, $R^{11}$ and $R^{12}$ have the same meaning as in formula (III).

5. A process according to claim 1, wherein the compound of formula (IV) is 1,1,4a,6-tetramethyl-5-methylenedecahydronaphthalene in the form of an essentially pure stereoisomer or in the form of a mixture of stereoisomers.

6. A process according to claim 1, wherein compound of formula $R^1CHO$ is paraformaldehyde.

7. A process according to claim 1, wherein temperature at which the reaction can be carried out is comprised in the range between 160° C. and 230° C.

8. A process for the preparation of a compound of formula (I)

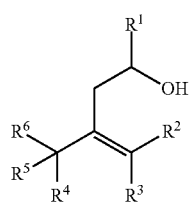

(I)

wherein $R^1$ represents a hydrogen atom or a $C_{1-8}$ alkyl group;

each $R^2$, $R^3$, $R^4$, $R^5$ represent, when taken separately, independently from each other, a $C_{1-9}$ linear, branched or cyclic alkyl group optionally substituted by one to two $C_{1-5}$ alkyl groups and optionally comprising one or two functional groups of an ether, ester, carbonyl, amine, amide or alcohol group; $R^2$ and $R^3$, when taken together, represent a $C_{4-11}$ linear, branched or cyclic alkanediyl group optionally comprising one or two functional groups of an ether, ester, carbonyl, amine, amide or alcohol group and/or $R^3$ and $R^4$, when taken together, represent a $C_{2-9}$ linear, branched or cyclic alkanediyl group and/or $R^4$ and $R^5$, when taken together, represent a $C_{4-9}$ linear, branched or cyclic alkanediyl group and/or $R^2$ and $R^5$, when taken together, represent a $C_{2-9}$ linear, branched or cyclic alkanediyl group; and $R^6$ represents a $C_{1-3}$ linear or branched alkyl group;

in the form of any one of its stereoisomers or a mixture thereof;

said process comprising the step of reacting a corresponding compound of formula (II)

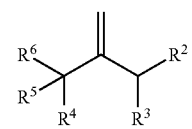

(II)

wherein $R^2$, $R^3$, $R^4$, $R^5$ and $R^6$ have the same meaning as in formula (I)

with a compound of formula $R^1CHO$, wherein $R^1$ has the same meaning as in formula (I), wherein the process is carried out in the presence of a carboxylic derivative of a $C_{2-8}$ carboxylic acid, $C_{4-16}$ carboxylic anhydride or a mixture of said carboxylic acid and said carboxylic anhydride.

9. A process according to claim 1, wherein the process is carried out in the presence of a solvent.

10. A process according to claim 8, wherein the compound of formula (II) are $C_9$-$C_{20}$ compounds.

11. A process according to claim 8, wherein the compound of formula (I) is compound of formula (III)

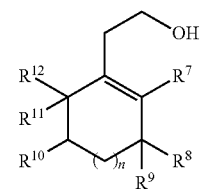

(III)

wherein n is 0 or 1;

each $R^8$, $R^9$, $R^{10}$ represent, when taken separately, independently from each other, a hydrogen atom or a $C_{1-6}$ linear, branched or cyclic alkyl group optionally substituted by one to two $C_{1-3}$ alkyl groups and optionally comprising one or two functional groups of an ether, ester, carbonyl, amine, amide or alcohol group;

each $R^7$, $R^{11}$, $R^{12}$ represent, when taken separately, independently from each other, a $C_{1-6}$ linear, branched or cyclic alkyl group optionally substituted by one to two $C_{1-3}$ alkyl groups and optionally comprising one or two functional groups of an ether, ester, carbonyl, amine, amide or alcohol group; $R^7$ and $R^8$, when taken together, represent a $C_{3-9}$ linear or branched alkanediyl group optionally comprising one or two functional groups of an ether, ester, carbonyl, amine, amide or alcohol group and/or $R^9$ and $R^{10}$, when taken together, represent a $C_{1-2}$ linear alkanediyl group and/or $R^{10}$ and $R^{11}$, when taken together, represent a $C_{3-9}$ linear or branched alkanediyl group and/or $R^8$ and $R^{11}$, when taken together, represent a $C_{1-3}$ linear or branched alkanediyl group; and $R^{12}$ represents a $C_{1-3}$ linear or branched alkyl group;

in the form of any one of its stereoisomers or a mixture thereof.

12. A process according to claim 8, wherein the compound of formula (II) is compound of formula (IV)

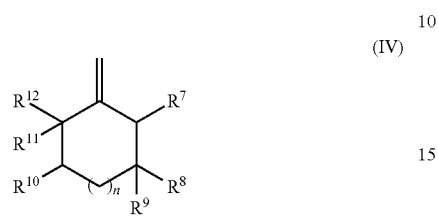

(IV)

wherein n, $R^7$, $R^8$, $R^9$, $R^{10}$, $R^{11}$ and $R^{12}$ have the same meaning as in formula (III).

13. A process according to claim 8, wherein the compound of formula (IV) is 1,1,4a,6-tetramethyl-5-methylene-decahydronaphthalene in the form of an essentially pure stereoisomer or in the form of a mixture of stereoisomers.

14. A process according to claim 8, wherein compound of formula $R^1CHO$ is paraformaldehyde.

15. A process according to claim 8, wherein temperature at which the reaction can be carried out is comprised in the range between 160° C. and 230° C.

16. A process according to claim 8, wherein the process is carried out in the presence of a solvent.

* * * * *